(12) United States Patent
Roe

(10) Patent No.: US 12,150,846 B2
(45) Date of Patent: Nov. 26, 2024

(54) ABSORBENT ARTICLE WITH FASTENING SYSTEM

(71) Applicant: The Procter & Gamble Company, Cincinnati, OH (US)

(72) Inventor: Donald Carroll Roe, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 785 days.

(21) Appl. No.: 17/173,453

(22) Filed: Feb. 11, 2021

(65) Prior Publication Data

US 2021/0251825 A1    Aug. 19, 2021

Related U.S. Application Data

(60) Provisional application No. 62/975,980, filed on Feb. 13, 2020.

(51) Int. Cl.
*A61F 13/62* (2006.01)
*A61F 13/511* (2006.01)

(52) U.S. Cl.
CPC ..... *A61F 13/62* (2013.01); *A61F 2013/51165* (2013.01)

(58) Field of Classification Search
CPC ............ A61F 13/62; A61F 2013/51165; A61F 13/625; A61F 13/622; A61F 13/627
See application file for complete search history.

(56) References Cited

U.S. PATENT DOCUMENTS

| 3,848,594 A | 11/1974 | Buell |
| 3,860,003 A | 1/1975 | Buell |
| 3,911,173 A | 10/1975 | Sprague, Jr. |
| 4,573,986 A | 3/1986 | Minetola |
| 4,610,678 A | 9/1986 | Weisman |
| 4,662,875 A | 5/1987 | Hirotsu |
| 4,673,402 A | 6/1987 | Weisman et al. |
| 4,785,996 A | 11/1988 | Ziecker |
| 4,834,735 A | 5/1989 | Alemany |

(Continued)

FOREIGN PATENT DOCUMENTS

| CN | 1328424 A | 12/2001 |
| CN | 1520265 A | 8/2004 |

(Continued)

OTHER PUBLICATIONS

PCT Search Report and Written Opinion for PCT/US2021/017558 dated Jun. 4, 2021, 11 pages.

(Continued)

*Primary Examiner* — Leslie A Lopez
*Assistant Examiner* — Nhu Q. Tran
(74) *Attorney, Agent, or Firm* — Daniel S. Albrecht

(57) ABSTRACT

An absorbent article includes a topsheet, a backsheet, and an absorbent core disposed between the topsheet and backsheet; and a fastening system. The fastening system has a fastening component disposed on an article component. A plurality of layers overlap at least a portion of the fastening component in an overlapping region. The fastening component includes a first plurality of fastening elements integrally formed from a first set of layers and a second plurality of fastening elements integrally formed from a second set of layers.

16 Claims, 10 Drawing Sheets

(56) References Cited

U.S. PATENT DOCUMENTS

| | | |
|---|---|---|
| 4,842,666 A | 6/1989 | Werenicz |
| 4,846,815 A | 7/1989 | Scripps |
| 4,850,992 A | 7/1989 | Amaral et al. |
| 4,888,231 A | 12/1989 | Angstadt |
| 4,894,060 A | 1/1990 | Nestegard |
| 4,946,527 A | 8/1990 | Battrell |
| 5,137,537 A | 8/1992 | Herron |
| 5,147,345 A | 9/1992 | Lavon |
| 5,151,092 A | 9/1992 | Buell |
| 5,156,793 A | 10/1992 | Buell |
| 5,167,897 A | 12/1992 | Weber |
| 5,221,274 A | 6/1993 | Buell |
| 5,242,436 A | 9/1993 | Weil |
| 5,260,345 A | 11/1993 | Desmarais |
| 5,342,338 A | 8/1994 | Roe |
| 5,387,207 A | 2/1995 | Dyer |
| 5,397,316 A | 3/1995 | Young |
| 5,518,801 A | 5/1996 | Chappell |
| 5,554,145 A | 9/1996 | Roe |
| 5,569,234 A | 10/1996 | Buell |
| 5,580,411 A | 12/1996 | Nease |
| 5,624,429 A | 4/1997 | Long et al. |
| 5,628,097 A | 5/1997 | Benson |
| 5,700,254 A | 12/1997 | Mcdowall |
| 5,778,457 A | 7/1998 | Conway |
| 5,993,432 A | 11/1999 | Lodge |
| 6,004,306 A | 12/1999 | Robles |
| 6,061,881 A | 5/2000 | Takizawa et al. |
| 6,120,487 A | 9/2000 | Ashton |
| 6,174,303 B1 | 1/2001 | Suprise et al. |
| 6,410,129 B2 | 6/2002 | Zhang |
| 6,432,098 B1 | 8/2002 | Kline |
| 6,468,257 B1 | 10/2002 | Ono et al. |
| 6,478,784 B1 | 11/2002 | Johnson et al. |
| 6,613,032 B2 | 9/2003 | Ronnberg et al. |
| 6,616,649 B1 | 9/2003 | Ismail |
| 6,677,258 B2 | 1/2004 | Carroll |
| 6,746,434 B2 | 6/2004 | Johnson et al. |
| 6,764,475 B1 | 7/2004 | Olson |
| 6,843,134 B2 | 1/2005 | Anderson |
| 6,878,647 B1 | 4/2005 | Rezai |
| 6,884,494 B1 | 4/2005 | Curro |
| 6,890,872 B2 | 5/2005 | Bond |
| 6,905,987 B2 | 6/2005 | Noda |
| 6,926,705 B1 | 8/2005 | Coates |
| 6,964,720 B2 | 11/2005 | Schneider |
| 7,060,149 B2 | 6/2006 | Ortega |
| 7,062,983 B2 | 6/2006 | Anderson |
| 7,211,531 B2 | 5/2007 | Schneider |
| 7,223,818 B2 | 5/2007 | Autran |
| 7,254,874 B2 | 8/2007 | Duffy |
| 7,264,615 B2 | 9/2007 | Sherrod et al. |
| 7,435,243 B2 | 10/2008 | Miyamoto |
| 7,806,883 B2 | 10/2010 | Fossum |
| 7,819,853 B2 | 10/2010 | Desai |
| 8,062,279 B2 | 11/2011 | Miyamoto |
| 8,435,223 B2 | 5/2013 | Roe |
| 8,496,640 B2 | 7/2013 | Molander |
| 8,546,641 B2 | 10/2013 | Roe |
| 8,618,350 B2 | 12/2013 | Mansfield |
| 8,636,710 B2 | 1/2014 | Ellingson et al. |
| 8,759,605 B2 | 6/2014 | Roe |
| 8,784,722 B2 | 7/2014 | Rocha |
| 8,795,809 B2 | 8/2014 | Mansfield |
| 8,808,263 B2 | 8/2014 | Roe |
| 8,834,442 B2 | 9/2014 | Miyake et al. |
| 8,932,273 B2 | 1/2015 | Roe |
| 8,939,957 B2 | 1/2015 | Raycheck |
| 8,998,870 B2 | 4/2015 | Roe |
| 9,011,398 B2 | 4/2015 | Johnston et al. |
| 9,011,402 B2 | 4/2015 | Roe |
| 9,078,789 B2 | 7/2015 | Wang |
| 9,089,456 B2 | 7/2015 | Roe |
| 9,339,425 B2 | 5/2016 | Stabelfeldt et al. |
| 9,387,138 B2 | 7/2016 | Roe |
| 9,597,237 B2 | 3/2017 | Enz |
| 9,849,043 B2 | 12/2017 | Barnes et al. |
| 10,076,162 B2 | 9/2018 | Rocha |
| 10,798,997 B2 | 10/2020 | Rocha |
| 11,426,312 B2 | 8/2022 | Collins et al. |
| 2002/0151858 A1 | 10/2002 | Karami |
| 2003/0119404 A1* | 6/2003 | Belau ............ A44B 18/0011 |
| | | 442/361 |
| 2005/0079321 A1* | 4/2005 | Tuman ............ A61F 13/625 |
| | | 428/100 |
| 2005/0164587 A1 | 7/2005 | Melik |
| 2006/0167432 A1 | 7/2006 | Sigari |
| 2006/0293639 A1 | 12/2006 | Van |
| 2007/0203301 A1 | 8/2007 | Autran |
| 2007/0219521 A1 | 9/2007 | Hird |
| 2007/0249254 A1 | 10/2007 | Mansfield |
| 2007/0287348 A1 | 12/2007 | Autran |
| 2007/0287983 A1 | 12/2007 | Lodge |
| 2007/0293111 A1 | 12/2007 | Mansfield |
| 2008/0045917 A1 | 2/2008 | Autran |
| 2008/0319407 A1 | 12/2008 | Trinkaus |
| 2009/0258210 A1 | 10/2009 | Iyad |
| 2010/0180407 A1 | 7/2010 | Rocha |
| 2011/0139657 A1 | 6/2011 | Hird |
| 2011/0139658 A1 | 6/2011 | Hird |
| 2011/0139659 A1 | 6/2011 | Hird |
| 2011/0144609 A1 | 6/2011 | Petersen et al. |
| 2011/0152812 A1 | 6/2011 | Hird |
| 2012/0022485 A1 | 1/2012 | Roe et al. |
| 2012/0022491 A1 | 1/2012 | Roe |
| 2013/0006209 A1 | 1/2013 | Ruiz |
| 2013/0082418 A1 | 4/2013 | Curro |
| 2013/0324959 A1 | 12/2013 | Ashraf et al. |
| 2014/0000003 A1 | 1/2014 | Ashraf et al. |
| 2014/0005621 A1 | 1/2014 | Roe |
| 2014/0012220 A1 | 1/2014 | Flieg |
| 2014/0257226 A1 | 9/2014 | Wang et al. |
| 2016/0136014 A1 | 5/2016 | Arora |
| 2017/0027775 A1* | 2/2017 | Barnes ............ A61F 13/622 |
| 2017/0181905 A1 | 6/2017 | Sakurai et al. |
| 2018/0042777 A1 | 2/2018 | Dalal |
| 2018/0042778 A1 | 2/2018 | Lenser |
| 2018/0050484 A1 | 2/2018 | Rocha |
| 2018/0228664 A1 | 8/2018 | Hou |
| 2018/0271716 A1 | 9/2018 | Dalal |
| 2018/0271717 A1 | 9/2018 | Dria |
| 2019/0209400 A1 | 7/2019 | Collins et al. |
| 2020/0179184 A1 | 6/2020 | Kaiser |
| 2021/0007912 A1* | 1/2021 | Swedberg ........ A61F 13/15756 |
| 2021/0251818 A1 | 8/2021 | Roe et al. |
| 2021/0251824 A1 | 8/2021 | Roe |
| 2021/0386601 A1 | 12/2021 | Hayden et al. |
| 2021/0386602 A1 | 12/2021 | Raycheck et al. |

FOREIGN PATENT DOCUMENTS

| | | |
|---|---|---|
| CN | 102341228 A | 2/2012 |
| CN | 102740820 A | 10/2012 |
| CN | 103068270 A | 4/2013 |
| CN | 204600915 U | 9/2015 |
| CN | 205053047 U | 3/2016 |
| CN | 107635747 A | 1/2018 |
| CN | 108703840 A | 10/2018 |
| EP | 0446818 A2 | 9/1991 |
| EP | 3481355 B1 | 8/2020 |
| JP | 2011156309 A | 8/2011 |
| JP | 2012050575 A | 3/2012 |
| JP | 2013212215 A | 10/2013 |
| JP | 2014094159 A | 5/2014 |
| WO | 9510996 A1 | 4/1995 |
| WO | 0015089 A1 | 3/2000 |
| WO | 0059430 A1 | 10/2000 |
| WO | 03003960 A2 | 1/2003 |
| WO | 02067809 A3 | 4/2003 |
| WO | WO-2011129097 A1 * | 10/2011 ......... A61F 13/5622 |
| WO | 2015167533 A2 | 11/2015 |
| WO | 2016085960 A1 | 6/2016 |

(56) References Cited

FOREIGN PATENT DOCUMENTS

| | | |
|---|---|---|
| WO | 2019043640 A1 | 3/2019 |
| WO | 2019120574 A1 | 6/2019 |
| WO | 2020041271 A1 | 2/2020 |

OTHER PUBLICATIONS

Final Office Action; U.S. Appl. No. 17/173,471 dated May 25, 2023.
Non-Final Office Action; U.S. Appl. No. 17/173,358 dated Sep. 27, 2023.
Non-Final Office Action; U.S. Appl. No. 17/173,471 dated Jan. 10, 2023.
Non-Final Office Action; U.S. Appl. No. 17/173,471 dated Oct. 4, 2023.

\* cited by examiner

ABSORBENT ARTICLE WITH FASTENING SYSTEM

CROSS REFERENCE TO RELATED APPLICATION

This application claims the benefit of U.S. Provisional Application No. 62/975,980, filed Feb. 13, 2020, the substances of which are incorporated herein by reference.

FIELD OF THE INVENTION

The present disclosure relates to absorbent articles having fastening systems, in particular, fastening systems having portions integrally formed from an article component.

BACKGROUND OF THE INVENTION

It has long been known that absorbent articles such as conventional absorbent articles (e.g., diapers, adult incontinence articles, feminine hygiene pads) offer the benefit of receiving and containing urine and/or other bodily exudates (e.g., feces, menses, mixture of feces and urine, mixture of menses and urine, etc.). To effectively contain bodily exudates, the article should provide a snug fit around the waist and legs of a wearer. Fastening systems have been used to ensure the article is secured about the wearer and remains in place. Typically, one or more fastening systems extend along the left and right longitudinal edges of the chassis in the waist regions. The fastening systems comprise components that engage such that the rear waist region may be joined to the front waist region about the waist of the wearer.

Fastening systems are often discrete from the article component to which they are attached. In this way, fastener suppliers provide strips or patches of fastening material (e.g., hook material or loops material) to the manufacturer of an article component or the manufacturer of a final article to be sold. The manufacturer may modify the fastening material strips/patches to suit size and other needs and affix the fastening material to the article component.

It has been proposed to form fastening material, in particular fastening elements such as hooks, directly on a preexisting substrate which forms part of the article component. Such techniques may provide a benefit of elimination of processing and handling steps. In addition, the article component or final article manufacturer may have direct design control over the fastening system. However, it is believed that improvements are still necessary for such techniques.

Indeed, there continues to be a need for flexibility in the design of fastening systems. There is a need for varied properties within a fastening system or between different fastening systems in the same article to, for example, better handle stresses of application and wear, effectuate different aesthetic designs, offer flexibility in material choice, and/or reduce costs by eliminating more expensive materials where they are not needed. Further, there is a continued need for fastening systems that require less material and can be made without undesirable complexity.

SUMMARY OF THE INVENTION

The invention comprises the features of the independent claims herein. An absorbent article comprises a topsheet, a backsheet, and an absorbent core disposed between the topsheet and backsheet; a first waist region, a second waist region and a crotch region disposed between the first and second waist region; and a fastening system comprising a fastening component disposed on an article component, wherein at least two layers overlap at least a portion of the fastening component and wherein the fastening component comprises a first plurality of fastening elements integrally formed from a first set of layers and a second plurality of fastening elements integrally formed from a second set of layers.

An absorbent article comprises a topsheet, a backsheet, and an absorbent core disposed between the topsheet and backsheet; a first waist region, a second waist region and a crotch region disposed between the first and second waist region; and a fastening system comprising a fastening component disposed on an article component, wherein at least two layers overlap at least a portion of the fastening component and wherein the fastening component comprises a first plurality of elements integrally formed from a first set of layers and a second plurality of elements disposed on a discrete patch.

An absorbent article comprises a chassis comprising a topsheet, a backsheet, and an absorbent core disposed between the topsheet and backsheet; a first waist region, a second waist region and a crotch region disposed between the first and second waist region; and a fastening component disposed on an article component and a plurality of layers overlapping the fastening component in an overlapping region, wherein:
the plurality of layers comprises a first material layer and a secondary layer, and
a plurality of integral fastening elements is integrally formed from the first material layer but not from the secondary layer.

DETAILED DESCRIPTION OF THE INVENTION

Definitions

Figure 1:
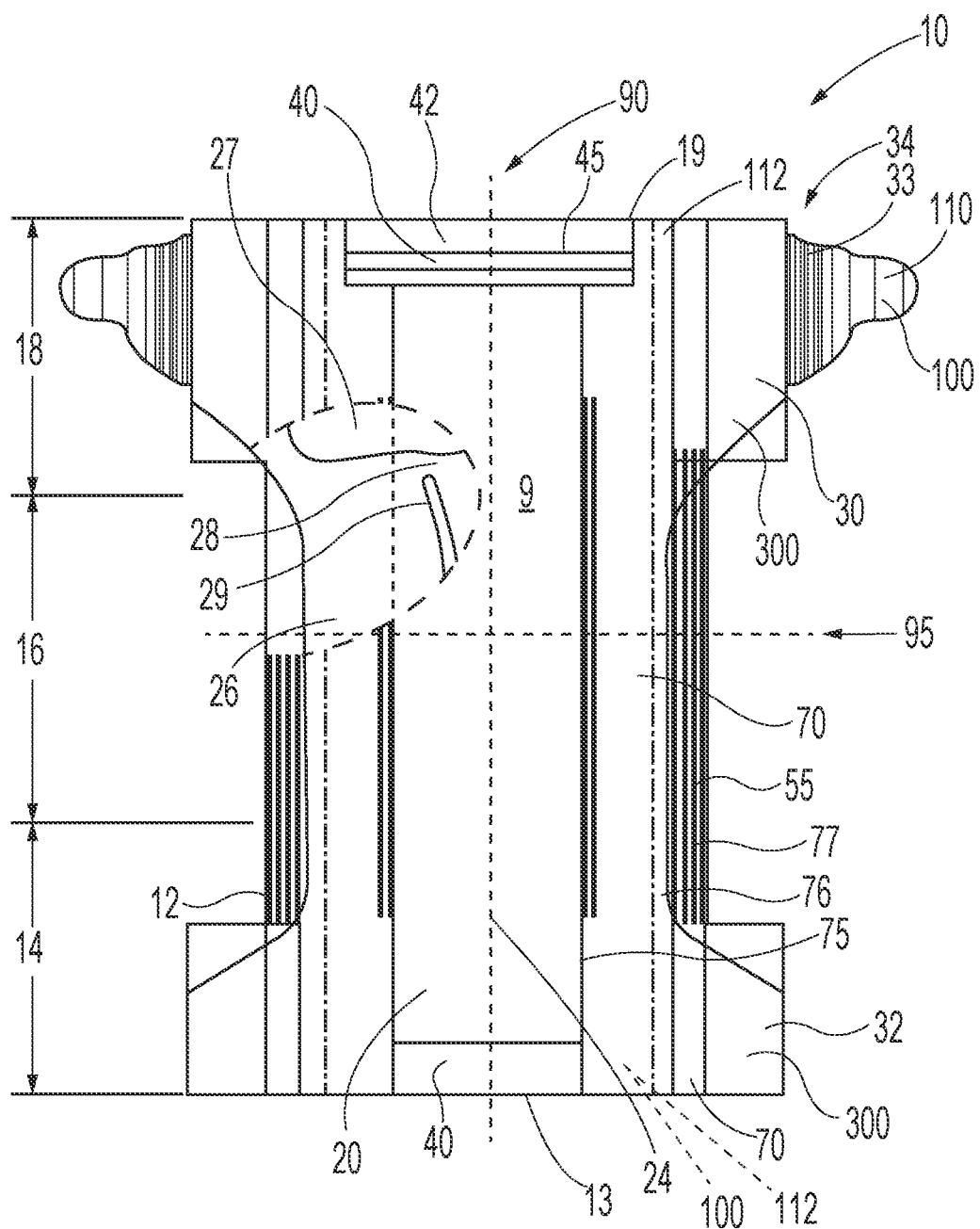
FIG. 1 is a schematic plan view of an exemplary absorbent article according to one nonlimiting embodiment of the present invention. The absorbent article is shown in a flat, uncontracted state.

"Absorbent article" means a device that absorbs and contains body exudates and, more specifically, devices that are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Design element" as used herein means a shape or combination of shapes that visually create a distinct and discrete form, regardless of the size or orientation of the form. Design elements may comprise insignia. Design elements and/or combinations of design elements may comprise letters, words and/or graphics such as flowers, butterflies, hearts, character representations and the like. Design elements and/or combinations of design elements may comprise instructional indicia providing guidance or instruction to the caregiver relative to placement and/or fit of the article about the wearer.

"Insignia" as used herein means objects, character representations, words, colors, shapes or other indicia that can be used to distinguish, identify or represent the manufacturer, retailer, distributor and/or brand of a product, including but not limited to trademarks, logos, emblems, symbols, designs, figures, fonts, lettering, crests or similar identifying marks.

"Disposable," in reference to articles, means that the articles are generally not intended to be laundered or otherwise restored or reused in the same capacity (i.e., they are intended to be discarded after a single use and, preferably, to be recycled, composted or otherwise discarded in an environmentally compatible manner).

"Disposed" refers to an element being located in a particular place or position. A feature that is disposed on a surface or side of a component may be integral with said component or may be joined to said component.

"Elastic" and "elastomeric" mean the ability of a material to stretch by at least 50% without rupture or breakage at a given load, and upon release of the load the elastic material or component exhibits at least 70% recovery (i.e., has less than 30% set) in one of the directions as per the Hysteresis Test described herein. Stretch, sometimes referred to as strain, percent strain, engineering strain, draw ratio, or elongation, along with recovery and set may each be determined according to the Hysteresis Test described in more detail below.

"Extensible" means the ability to stretch or elongate, without rupture or breakage, by at least 50% as per step 6(a) in the Hysteresis Test herein.

"Inboard," with respect to a first feature of an article and its position relative a second feature or location on the article, means that the first feature lies closer to a respective axis of the article than the second feature or location, along a horizontal x-y plane approximately occupied by the article when laid out flat, extended to the full longitudinal and lateral dimensions of its component web materials against any contraction induced by any included pre-strained elastomeric material, on a horizontal surface. Laterally inboard means the first feature is closer to the longitudinal axis, and longitudinally inboard means the first feature is closer to the lateral axis. Conversely, "outboard," with respect to a first feature of an article and its position relative a second feature or location on the article, means that the first feature lies farther from the respective axis of the article than the second feature or location.

"Integral" means configurations whereby an element is created from or created by an article component, or portions thereof, as opposed to being joined to the component. "Integrally formed" means an element is created from an underlying material or portion thereof, by for example molding, shaping and/or reconstituting the material.

"Joined" means configurations whereby an element is directly secured to another element by affixing the element directly to the other element, and configurations whereby an element is indirectly secured to another element by affixing the element to intermediate member(s) that in turn are affixed to the other element.

"Longitudinal" means a direction lengthwise in a component such that the longitudinal direction runs parallel to the maximum linear dimension in the x-y plane of the component. In an absorbent article as described herein, the longitudinal direction runs substantially perpendicular from a waist end edge to an opposing waist end edge when the absorbent article is in a flat out, uncontracted state, or from a waist end edge to the bottom of the crotch in a bifolded article.

"Lateral" refers to a direction generally perpendicular to the longitudinal direction. In the absorbent article described herein, the lateral direction runs substantially parallel from a side edge to an opposing side edge.

Overview

FIG. 1 is a plan view of an exemplary, nonlimiting embodiment of an absorbent article 10 of the present invention in a flat, uncontracted state. The article may be disposable. The body-facing surface 9 of the absorbent article 10 is facing the viewer. The absorbent article 10 comprises a chassis 20. The absorbent article 10 and chassis 20 are shown to have a first waist region 14, a second waist region 18 opposed to the first waist region 14, and a crotch region 16 located between the first waist region 14 and the second waist region 18. The waist regions 14 and 18 generally comprise those portions of the absorbent article which, when worn, encircle the waist of the wearer.

Figure 2:
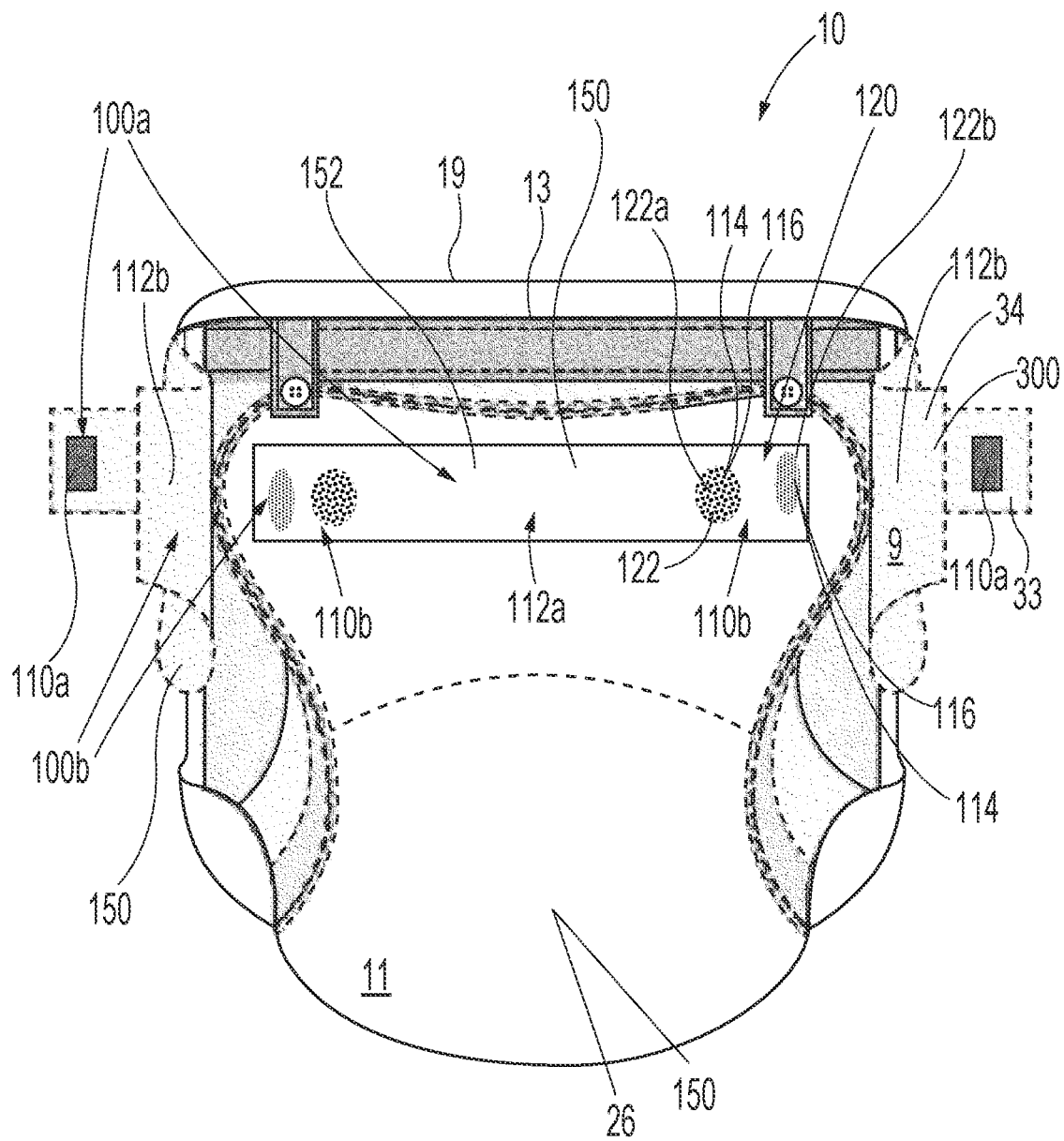
FIG. 2 is a schematic front elevation view of an exemplary absorbent article according to a nonlimiting embodiment. The absorbent article is shown in a folded state.

As shown for example in FIG. 2, the article may comprise one or more fastening systems 100, such as a primary fastening system 100a and a secondary fastening system 100b in the waist regions. The fastening systems may each comprise a fastening component 110 and a receiving component 112 (identified with an 'a' and 'b' in FIG. 2 with reference to their respective fastening systems). The fastening component 110 comprises fastening elements 114, which may be in the form of hooks 116. The fastening elements 114 may be integral with one or more layers of the article component 150 on which the fastening component is disposed. In certain embodiments, fastening elements may be formed from different underlying substrates. These and other details of the invention are disclosed more completely below.

Absorbent Article

Returning to FIG. 1, the absorbent article 10 includes a longitudinal centerline 90 and a lateral centerline 95. The outer periphery of the chassis 20 is defined by longitudinal edges 12 and waist edges (first waist edge 13 in first waist region 14 and second waist edge 19 in second waist region 18). The chassis 20 may have opposing longitudinal edges 12 that are oriented generally parallel to the longitudinal centerline 90. However, for better fit, longitudinal edges 12 may be curved or angled to produce, for example, an "hourglass" shape article when viewed in a plan view as shown in FIG. 1. The chassis 20 may have opposing lateral edges 13, 19 (i.e., the first waist edge 13 and second waist edge 19) that are oriented generally parallel to the lateral centerline 95.

The chassis 20 may comprise a liquid permeable topsheet 24, a backsheet 26, and an absorbent core 28 between the topsheet 24 and the backsheet 26. The absorbent core may comprise absorbent material, including for example superabsorbent particles and absorbent gelling materials (AGM). The topsheet 24 may be joined to the core 28 and/or the backsheet 26. The backsheet 26 may be joined to the core 28 and/or the topsheet 24. It should be recognized that other structures, elements, or substrates may be positioned between the core 28 and the topsheet 24 and/or backsheet 26. In some embodiments, an acquisition-distribution system 27 is disposed between the topsheet 24 and the absorbent core 28.

In certain embodiments, the chassis 20 comprises the main structure of the absorbent article 10 with other features added to form the composite absorbent article structure. While the topsheet 24, the backsheet 26, and the absorbent core 28 may be assembled in a variety of well-known configurations, absorbent article configurations are described generally in U.S. Pat. Nos. 3,860,003; 5,151,092; 5,221,274; 5,554,145; 5,569,234; 5,580,411; and 6,004,306. One or more masking layers or materials may be provided in the absorbent article. A masking layer may be a layer that provides a cushiony feel when the absorbent article is touched from the garment-facing surface or the wearer-facing surface. The masking layer may "mask" a grainy feel potentially caused by the absorbent material, such as superabsorbent polymers. The masking layer may "mask" bodily exudates from being visible when viewing the wearer-facing surface or the garment-facing surface of the absorbent article. The masking layer may have a basis weight in the range of about 15 gsm to about 50 gsm or about 15 gsm to about 40 gsm. The masking layer may comprise one or more nonwoven materials (e.g., a hydroentangled nonwoven material), foams, pulp layers, and/or other suitable materials. The masking layer may be the outer cover material of the backsheet. The masking layer may be the layer forming the garment-facing side or the wearer-facing side of the core. The masking layer may be a separate material positioned intermediate the garment-facing side of the core and the liquid impermeable backsheet.

Components of the disposable absorbent article can at least partially be comprised of bio-sourced content as described in U.S. Pat. Pub. Nos. 2007/0219521A1, 2011/0139658A1, 2011/0139657A1, 2011/0152812A1, and 2011/0139659A1. These components include, but are not limited to, topsheets, backsheet films, backsheet nonwovens, side panels, leg gasketing systems, superabsorbent, acquisition layers, core wrap materials, adhesives, fastener systems, and landing zones. In at least one embodiment, a disposable absorbent article component comprises a bio-based content value from about 10% to about 100%, or from about 25% to about 75%, or from about 50% to about 60% using ASTM D6866-10, method B. In order to apply the methodology of ASTM D6866-10 to determine the bio-based content of any component, a representative sample of the component must be obtained for testing. In at least one embodiment, the disposable absorbent article component can be ground into particulates less than about 20 mesh using known grinding methods (e.g., WILEY® mill), and a representative sample of suitable mass taken from the randomly mixed particles.

Topsheet

The topsheet 24 is generally a portion of the absorbent article 10 that may be positioned at least in partial contact or close proximity to a wearer. Suitable topsheets 24 are generally supple, soft feeling, and non-irritating to a wearer's skin. Further, at least a portion of, or all of, the topsheet may be liquid permeable, permitting liquid bodily exudates to readily penetrate through its thickness. A suitable topsheet may be manufactured from a wide range of materials, such as porous foams, reticulated foams, apertured plastic films, woven materials, nonwoven materials, woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. The topsheet may have one or more layers. The topsheet may be apertured, may have any suitable three-dimensional features, and/or may have a plurality of embossments (e.g., a bond pattern). The topsheet may be apertured by overbonding a material and then rupturing the overbonds through ring rolling, such as disclosed in U.S. Pat. No. 5,628,097, to Benson et al., issued on May 13, 1997 and disclosed in U.S. Pat. Appl. Publication No. US 2016/0136014 to Arora et al. Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet.

Absorbent Core

The absorbent core 28 may comprise a wide variety of liquid-absorbent materials commonly used in disposable diapers and other absorbent articles. Examples of suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials (AGM); or any other known absorbent material or combinations of materials. In certain embodiments, at least a portion of the absorbent core is substantially cellulose free and contains less than 10% by weight cellulosic fibers, less than 5% cellulosic fibers, less than 1% cellulosic fibers, no more than an immaterial amount of cellulosic fibers or no cellulosic fibers. It should be understood that an immaterial amount of cellulosic material docs not materially affect at least one of the thinness, flexibility, and absorbency of the portion of the absorbent core that is substantially cellulose free. Among other benefits, it is believed that when at least a portion of the absorbent core is substantially cellulose free, this portion of the absorbent core is significantly thinner and more flexible than a similar absorbent core that includes more than 10% by weight of cellulosic fibers. The amount of absorbent material, such as absorbent particulate polymer material present in the absorbent core may vary, but in certain embodiments, is present in the absorbent core in an amount greater than about 80%, or greater than about 85%, or greater than about 90%, or greater than about 95% by weight of the core. In some embodiments, the absorbent core may comprise one or more channels 29, wherein said channels are substantially free of absorbent particulate polymer material. The channels 29 may extend longitudinally or laterally. The absorbent core may further comprise two or more channels. The channels may be straight, curvilinear, angled or any workable combination thereof. In nonlimiting examples, two channels are symmetrically disposed about the longitudinal axis. Exemplary absorbent structures for use as the absorbent core 28 are described in U.S. Pat. Nos. 4,610,678; 4,673,402; 4,834,735; 4,888,231; 5,137,537; 5,147,345; 5,342,338; 5,260,345; 5,387,207; 5,397,316, and U.S. patent application Ser. Nos. 13/491,642 and 15/232,901.

Backsheet

The backsheet 26 is generally positioned such that it may be at least a portion of the garment-facing surface 11 of the absorbent article 10 as shown in FIG. 2. Backsheet 26 may be designed to prevent the exudates absorbed by and contained within the absorbent article 10 from soiling articles that may contact the absorbent article 10, such as bed sheets and undergarments. In certain embodiments, the backsheet 26 is substantially water-impermeable. The backsheet may, for example, be or comprise a thin plastic film, such as a thermoplastic film having a thickness of about 0.012 mm to about 0.051 mm. Other suitable backsheet 26 materials may include breathable materials that permit vapors to escape from the absorbent article 10 while still preventing exudates from passing through the backsheet 26.

Backsheet 26 may also consist of more than one layer. The backsheet 26 may comprise an outer cover and an inner layer. The outer cover may be made of a soft, nonwoven material. The inner layer may be made of a substantially liquid-impermeable film, such as a polymeric film. The outer cover and an inner layer may be joined together by adhesive or any other suitable material or method. The outer cover material may comprise a bond pattern, apertures, and/or three-dimensional features. The outer cover may be a hydroentangled nonwoven material.

Lateral Extension Elements

Figure 3:
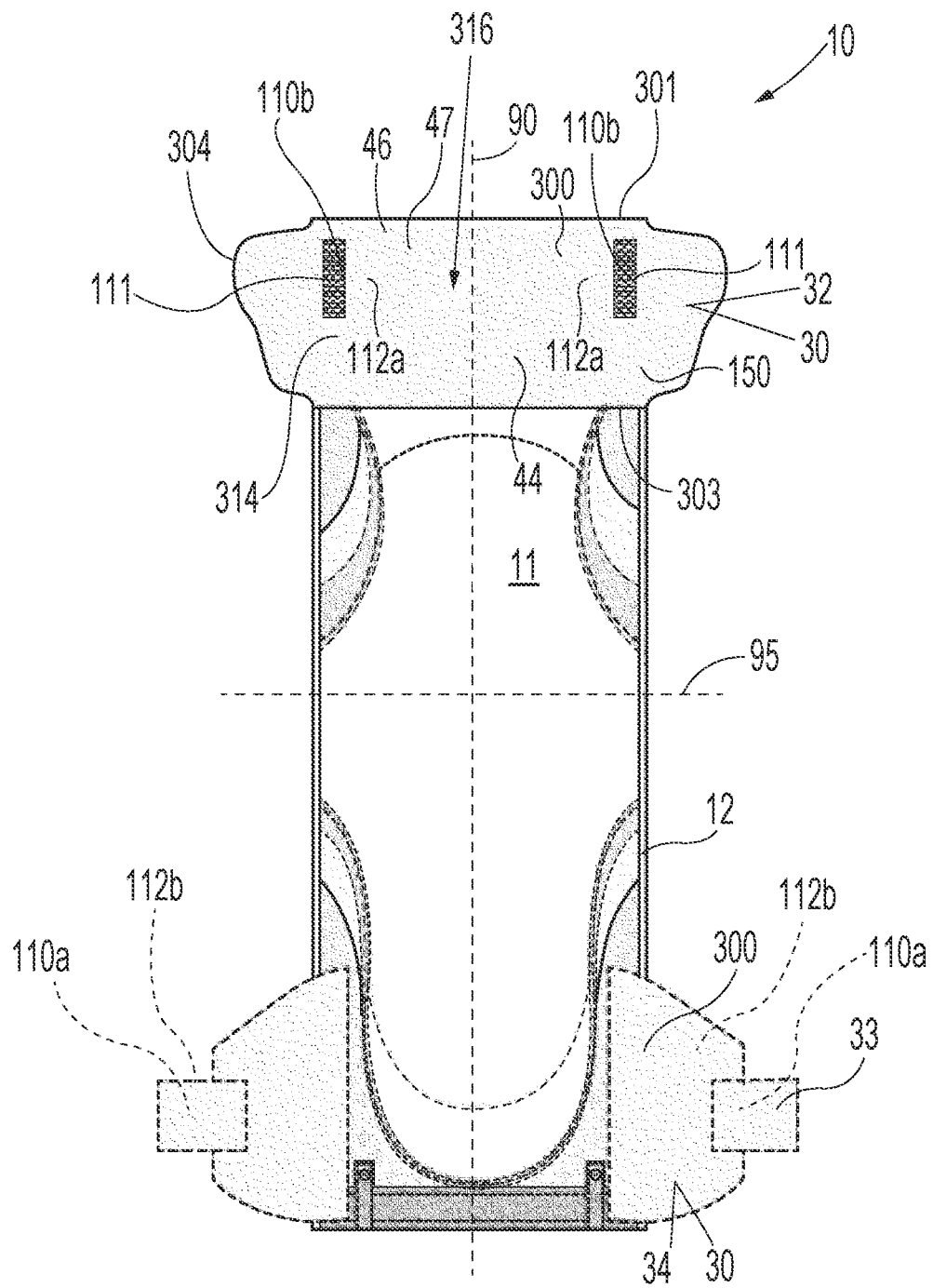
FIG. 3 is a schematic plan view of an exemplary absorbent article according to a nonlimiting embodiment. The absorbent article is shown in a flat, uncontracted state.

As shown in FIG. 1, the absorbent article 10 may include one or more lateral extension elements 300 (i.e., an element that extends laterally outboard of the longitudinal edge 12 of the chassis). The lateral extension element 300 may be disposed in a waist region. Nonlimiting examples of lateral extension elements include cars 30, belts 44 (which also cover a longitudinally central portion of a waist region), fastener attachment arms 33 and workable combinations thereof. Turning to FIG. 3, the lateral extension element 300 may comprise an outboard lateral edge 301, an inboard lateral edge 303, and outboard longitudinal edges 304.

In certain embodiments, the article 10 includes one or more lateral extension elements in the form of an ear 30, including for example front cars 32 disposed in the first waist region and/or back cars 34 disposed in the second waist region. An ear 30 may be integral with the chassis or a discrete element joined to the chassis 20. An ear 30 may be extensible or elastic. An ear 30 may be formed from one or more nonwoven webs, woven webs, knitted fabrics, polymeric and elastomeric films, apertured films, sponges, foams, scrims or combinations and/or laminates of any the foregoing.

In some embodiments, an ear 30 may include elastomers, such that the ear is stretchable. In certain embodiments, an ear 30 may be formed of a stretch laminate such as a nonwoven/elastomeric material laminate or a nonwoven/elastomeric material/nonwoven laminate, which also results in the car being stretchable. The ear 30 may be extensible in the lateral direction of the article. In some embodiments, the ear is elastic in the lateral direction. In further embodiments, the ear 30 may extend more in the lateral direction than in the longitudinal direction. Alternatively, the ear may extend more in the longitudinal direction than in the lateral direction. In certain nonlimiting examples, the ear may include one or more inelastic regions along with a separate elastic region. In some embodiments, the area of the elastic region comprises at least about 20%, or from about 30% to about 80%, of the total area of the car, reciting for said range every 5% increment therein. An inelastic region may be disposed laterally outboard of an elastic region. In nonlimiting examples, an elastic region is disposed between two inelastic regions.

Any suitable nonwoven may be used in an ear 30. Suitable nonwovens may comprise a basis weight of at least about 8 gsm, or less than about 22 gsm, or about 17 gsm or less, or from about 10 gsm to about 20 gsm, reciting for said range every 1 increment therein. Where the ear 30 comprises more than one nonwoven, the nonwovens may comprise the same basis weight or different basis weights. Likewise, the nonwovens may comprise the same layer structure or different layer structures. Further, a nonwoven in the ear may comprise the same or different features of nonwovens in the backsheet, topsheet, leg gasketing system and/or waist feature.

Nonlimiting examples of suitable elastomeric materials include film (e.g., polyurethane films, films derived from rubber and/or other polymeric materials), an elastomeric coating applied to another substrate (e.g., a hot melt elastomer, an elastomeric adhesive, printed elastomer or elastomer co-extruded to another substrate), elastomeric nonwovens, scrims, strands and the like. Elastomeric materials can be formed from elastomeric polymers including polymers comprising styrene derivatives, polyesters, polyurethanes, polyether amides, polyolefins, combinations thereof or any suitable known elastomers including but not limited to co-extruded VISTAMAXX®. Exemplary elastomers and/or elastomeric materials are disclosed in U.S. Pat. Nos. 8,618,350; 6,410,129; 7,819,853; 8,795,809; 7,806,883; 6,677,258 and U.S. Pat. Pub. No. 2009/0258210. Commercially available elastomeric materials include KRATON (styrenic block copolymer; available from the Kraton Chemical Company, Houston, TX), SEPTON (styrenic block copolymer; available from Kuraray America, Inc., New York, NY), VECTOR (styrenic block copolymer; available from TSRC Dexco Chemical Company, Houston, TX), ESTANE (polyurethane; available from Lubrizol, Inc, Ohio), PEBAX (polyether block amide; available from Arkema Chemicals, Philadelphia, PA), HYTREL (polyester; available from DuPont, Wilmington, DE), VISTAMAXX (homopolyolefins and random copolymers, and blends of random copolymers, available from EXXON Mobile, Spring, TX) and VERSIFY (homopolyolefins and random copolymers, and blends of random copolymers, available from Dow Chemical Company, Midland, Michigan).

The ear may be activated by processes disclosed in U.S. Pat. Pub. No. 2013/0082418, U.S. Pat. Nos. 5,167,897; 5,993,432; 5,156,793; 5,167,897; 7,062,983 and 6,843,134 for example. Alternatively, the ear 30 comprises a gathered laminate, wherein one of the layers is strained to a greater degree than a remaining layer during lamination and/or bonding. In this way, the less extensible layer (i.e., a nonwoven) will form gathers when the laminate is in a relaxed state. Corrugations then form in the nonwoven layer(s) when the subsequently formed laminate is in a relaxed state. The ear may comprise an ultrasonically bonded laminate as is disclosed for example in U.S. Pat. Pub. Nos. 2018/0042777, 2018/0042778; 2018/0271716; and 2018/0271717.

Where an article 10 comprises multiple cars 30, said cars 30 may be the same or may be different. By way of nonlimiting example, a back ear 34 may comprise an elastic ear while a front car 32 may be inelastic. Additionally, or alternatively, layers of a front ear may be joined by different means than layers of a back car. For example, the front ear layers may be joined by adhesive, and back ear layers may be joined by ultrasonic bonds.

In some embodiments, a lateral extension element may be in the form of a belt such that it also constitutes a waist feature. The lateral extension element 300 may comprise a combination belt structure 46, formed from a web material 47, which extends through the waist region and laterally outboard of the longitudinal edges of the chassis as shown in FIG. 3 for example. By combination belt structure 46, it is meant that the element is configured to both (i) provide and/or support a receiving component of a fastening system (discussed below) and (ii) form one or more cars 30 that extend outboard of a longitudinal edge 12 of the chassis. In the nonlimiting example shown in FIG. 3, the combination belt structure 46 is configured to provide and/or support receiving components 112a of a primary fastening system 100a as well as fastening components 110b of a secondary fastening system 100b, each of which is discussed below.

Without being bound by theory, it is believed that the combination belt structure prevents waste and reduces manufacturing costs and complexity as compared to cars. For example, known absorbent articles include front cars formed from extensions of one or more of the backsheet and topsheet materials, or alternatively, separate sections of material bonded to one or more of the topsheet, backsheet and/or cuff structure so as to extend laterally from the left and right sides of the chassis. Where the front cars are extensions of one or more of the backsheet and topsheet materials, manufacturing necessarily includes a profiled cutting of these materials to provide the extending front car portions, and associated material waste. When the front cars are formed of separate sections of material bonded to one or more of the topsheet, backsheet and/or cuff structure, manufacturing must include steps associated with placing and bonding these front ear components to the chassis. As an alternative, however, a section of web material 47 used to form a primary receiving component 112 of a primary fastening system may be selected so as to also to be suitable to form and provide one or more front cars 32, when cut to a size which allows for the section of web material to extend laterally beyond the chassis along the longitudinal side(s). In one example, the section of web material may be a section of nonwoven web material adapted to fastenably engage hooks included as or with primary fastening components 110, and thereby serve as the loops receiving component 112 of a hook-and-loop primary fastening system. In a more particular example, the section of nonwoven web material may be pattern bonded in a pattern of thermal bonds configured to enhance the strength and reliability of the material, and of the loops structures it provides. Suitable pattern bonding is disclosed in U.S. patent application Ser. No. 16/575,424. Not only does the combination belt structure provide a dual use as described, but the inclusion of the web material 47 to supplement the other materials of the chassis provides apparent and actual added lateral tensile strength, bending resistance, caliper and robustness to the waist region.

Fasteners

Returning to FIG. 2, the absorbent article 10 may also include one or more fastening systems 100. When fastened, a fastening system 100 may interconnect the first waist region 14 and the rear waist region 18 resulting in a waist circumference that may encircle the wearer during wear of the absorbent article 10. Each fastening system may comprise a fastening component 110 and a receiving component 112. A receiving component is operatively engageable with a fastening component. Nonlimiting examples of engageable fastening and receiving components include tape tabs, hook and loop fastening components, interlocking fasteners such as tabs & slots, buckles, buttons, snaps, and/or hermaphroditic fastening components. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. The fastening component and/or the receiving component may further include a release tape or other material, including folded material, that protects the component from insult prior to use. Fastening and receiving components may each be any suitable shape or size. A fastening component and receiving component that are engageable may be disposed on opposite surfaces of the article.

FIG. 2 shows an embodiment having two fastening systems 100a, 100b, each of which may be disposed in the waist region and used to secure the article about the waist and hips of the wearer. The primary fastening system 100a is shown to have a fastening component 110a on the wearer-facing surface 9 in the rear waist region and a receiving component 112a on the garment-facing surface 11 in the first waist region. The secondary fastening system 100b is shown to have a fastening component 110b on the garment-facing surface 11 of the first waist region and a receiving component 112b on the wearer-facing surface 9 of the second waist region. The fastening systems may comprise components on both the left and right sides of the article, which components may or may not be the same (e.g. types of fastening elements may be different). The use of two fastening systems can provide a greater surface area for fastening, and thereby de-concentrate lateral tensile forces communicated through the fastening location(s) as the rear waist region is pulled toward the front waist region, and vice versa, when the diaper is worn. In addition, having two distinct fastening locations reduces the tendency of the front portion of the article to pivot around a single fastening location. Further, the secondary system helps to create a line of tension closer to the front waist edge, which may reduce the likelihood of folding or flipping over of the front waist edge during wear. Further still, the secondary system may create an anchoring geodesic to direct forces from the crotch region to over the hips in order to prevent sagging during wearer.

Although shown in the waist regions, a fastening system may be used to facilitate closing or wrapping the article during disposal, securing the article to itself and/or securing the article to another surface such as a garment. Accordingly, fastening components and receiving components may be disposed at any suitable position or surface of the article.

In certain embodiments, a fastening component may be longitudinally offset from a lateral edge of the article component on which the fastening component is disposed. In an embodiment shown in FIG. 3 for example, the fastening component 110 may be longitudinally offset from an outboard lateral edge 301 of a lateral extension element by at least about 1 mm, or at least about 3 mm, or at least about 5 mm, or from about 1 mm to about 10 mm, reciting for said range every 0.5 mm increment therein. In nonlimiting examples, a fastening component does not coincide with any lateral edge of the component to which it is attached. It may be desired, for example, that fastening component 110 is disposed with its surface area and outer edges entirely within the surface area and outer edges of the lateral extension element, or other article component, to which it is joined.

Additionally, or alternatively, a fastening component may be laterally offset from a longitudinal edge of an article component on which it is disposed. For instance, as shown in FIG. 3, an outboard edge 111 of a fastening component 110 may be laterally inboard of a longitudinal edge 304 of a lateral extension element by at least about 1 mm, or at least about 3 mm, or at least about 5 mm, or from about 1 mm to about 10 mm, reciting for said range every 0.5 mm increment therein. In nonlimiting examples, the outboard edge 111 of the fastening component may be laterally inboard of a chassis edge 12.

One or more portions of a fastening system may be formed from, or may be joined to, a lateral extension element 300. Additionally, or alternatively, portions of the fastening system may be formed from, or may be joined to, the chassis 20. In embodiments where the portions of the fastening system are joined to the chassis, said portions may be joined to an exterior surface or between layers. In embodiments where portions of the fastening system are integral, said portions may be integral with any suitable surface.

A fastening component 110 comprises one or more fastening elements 114 which cause the component to engage with another surface, such as the receiving component. In various embodiments, fastening elements comprise hooks 116. Receiving component 112 comprises material adapted to fastenably cooperate with fastening elements, such as a section or patch adapted to serve as cooperative loops material, to provide a hook-and-loop fastening system combination. The fastening and/or receiving components may be discrete from and joined to article components 150 or may be integral with one or more article components 150. Article components 150 may be selected from the chassis 20, topsheet 24, backsheet 26, a lateral extension element 300, an ear 30, a landing zone 152 (i.e., a substrate or portion of the chassis comprising a receiving component), a fastener attachment arm 33, a waist feature 40, a combination belt structure 46 or combinations thereof. In nonlimiting examples, material forming a portion of an article component (such as nonwoven material forming portions of the combination belt structure) may comprise integral loops material as illustrated in FIG. 3. In further nonlimiting examples, fastening components and receiving components may be formed on the same patch of material. For example, a fastening component may be integrally formed from a combination belt structure 46 as shown in FIGS. 2-3.

Figure 4:
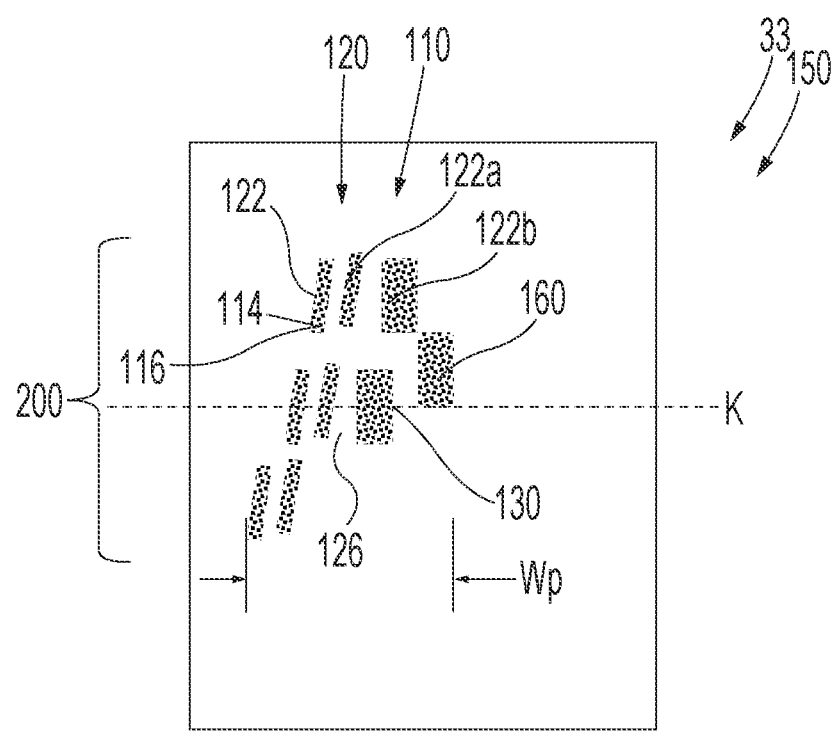
FIG. 4 is a plan view of a component comprising a fastening component disposed in a macro pattern.

Turning to FIG. 4, a fastening component 110 is disposed on an article component 150 in an overlapping region 200. In some embodiments, the fastening component 110 may be separately applied sections or patches 160 of fastening elements 114 that are bonded to article component by heat, compression, adhesive, ultrasonic bonding or any combination thereof.

In other examples, a fastening component may be a plurality of integral fastening elements 130, i.e. fastening elements 114 that are formed directly from one or more underlying layers 140. For example, fastening hooks 116 may be produced via application of molten polymer resin onto the layer, and subsequent formation of hooks in and from the melted, applied resin via known methods. The fastening components may be integrally formed from polymeric material by heating and softening a portion of the material and pressing it into hook-forming cavities, as is disclosed in U.S. Pat. No. 8,784,722. The fastening components may be integrally formed from the polymeric material through a single continuous process as is disclosed in commonly assigned U.S. patent application Ser. No. 16/545,425. Hooks-forming cavities may be formed and arranged on a hooks-forming roller in any desired configuration of hook size, shape, number, density, placement pattern, and arrangement of areas of hooks.

Figure 5A:
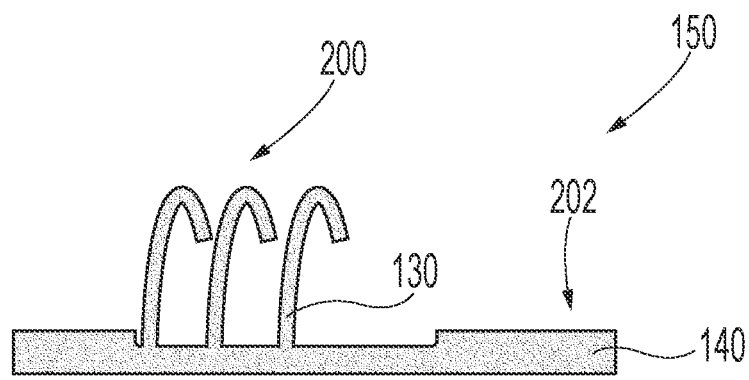
FIGS. 5A-5H are schematic side elevation views of exemplary hook configurations.
Figure 5B:
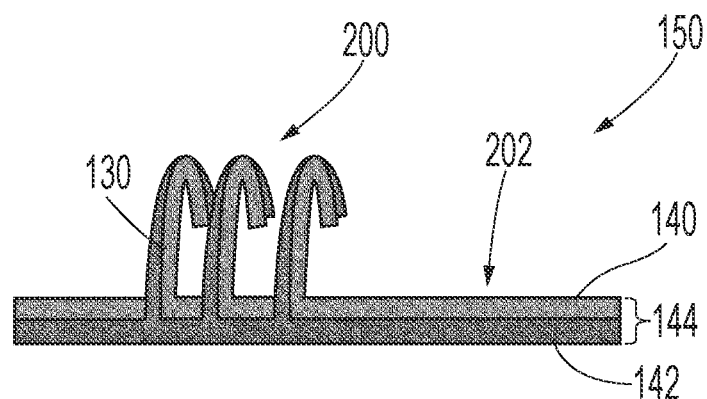

The fastening elements may be disposed in a macro pattern 120 having a plurality of arrays 122, including a first array 122a and a second array 122b of fastening elements. The macro pattern may optionally include additional arrays, such as a third array 122c as shown in FIGS. 6B-6C and discussed more fully below.

Where integrally formed, the fastening elements may be formed from one or more layers of the article component. Referring to FIG. 5A, in the overlapping region 200, the article component 150 may comprise a material layer 140. FIG. 5B illustrates an embodiment wherein the article component comprises a laminate 144 of a first material layer 140 and a second material layer 142. It is also contemplated that that the laminate may comprise three or more material layers. Integral fastening elements 130 may be formed from one material layer 140 of the absorbent article component 150 as suggested in FIG. 5A, or from multiple material layers 140, 142 of the article component 150 as is suggested in FIG. 5B.

Figure 5C:
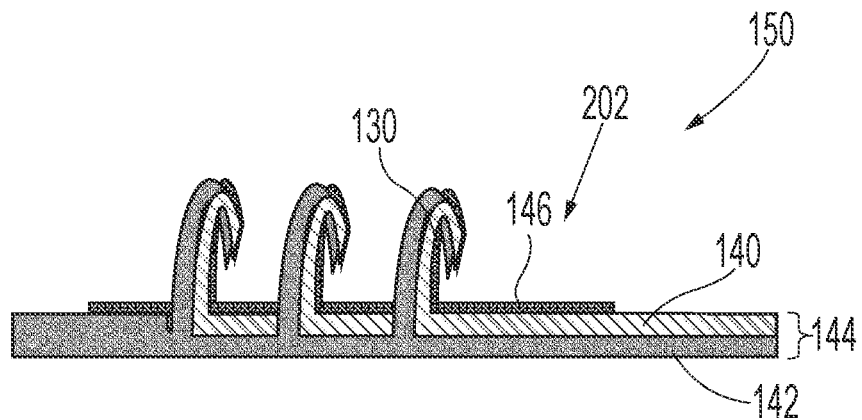

In certain embodiments, a further discrete material 146 from the article component may be included in the overlapping region, and integral fastening elements may be formed from one or more layers of the article component 140, 142 and the further discrete material 146 as indicated by FIG. 5C. For instance, when forming the integral fastening elements 130, the further discrete material may be joined to or positioned in overlapping relationship with the article component 150, and both the article component and the further discrete material may be heated and/or softened and pressed into hook forming cavities.

Layers and materials from which integral fastening elements may be formed may comprise a nonwoven, elastomer, film, polyolefin (e.g., polypropylene, polyethylene), adhesive, hotmelt composition (e.g., hotmelt adhesive, metallocene-catalyzed polymers (e.g., LICOCENE® from Clariant)), ink, dye, tactile modifier (e.g., silicone) and combinations thereof. A layer may be applied in a liquid state or in at least a partially molten state to the overlapping region. In various nonlimiting examples, fastening elements are formed from resilient yet conformable materials such as polypropylene and/or polyethylene. Such resilient materials permit the fastening materials to return to their desired configuration after use or other disruption. It is also contemplated that fastening elements in two different arrays may be made from different materials and/or different fastening elements within the same array may be made from different materials. For instance, one array may comprise fastening elements comprising stiffer materials such as nylon, polyolefins and biocomponent coextruded materials (e.g., polypropylene/polyethylene) and combinations thereof, while another array may comprise fastening elements formed from materials having lower modulus, which may also comprise polyolefins (i.e., lower modulus polyolefin). It may be desirable to have stiffer fasteners disposed centrally in the fastening component. For instance, the stiffer elements may be disposed about 5 mm from one or both longitudinal edges, such that the longitudinally inward section of the fastening component is stiffer than the edge. It is also contemplated that other variations can be used.

Figure 5D:
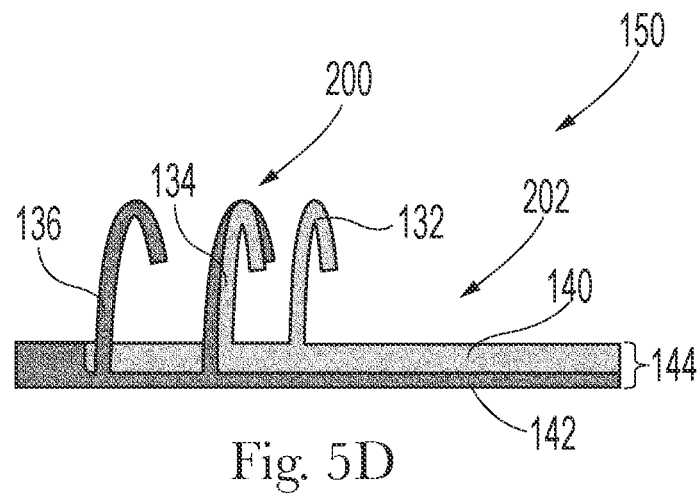

In some embodiments, two integral fastening elements may be formed from different material layers. For instance, referring to FIG. 5D, a first integral hook 132 may comprise material from the first material layer 140 but not the second material layer 142. A second integral hook 134 may comprise material from both the first and the second material layers 140, 142. A third integral hook 136 may comprise material from the second material layer 142 but not the first material layer 140. In other nonlimiting examples shown in FIGS. 5E-5F, a first plurality of fastening elements 138 may comprise integral elements 130 formed by a first set of layers S1, and a second plurality of fastening elements 139 may comprise integral elements 130 formed from a second set of layers S2. The second set of layers comprises at least one layer that is not present in the first set. It is to be appreciated that set, in this context, may include a single layer of material.

Figure 5E:
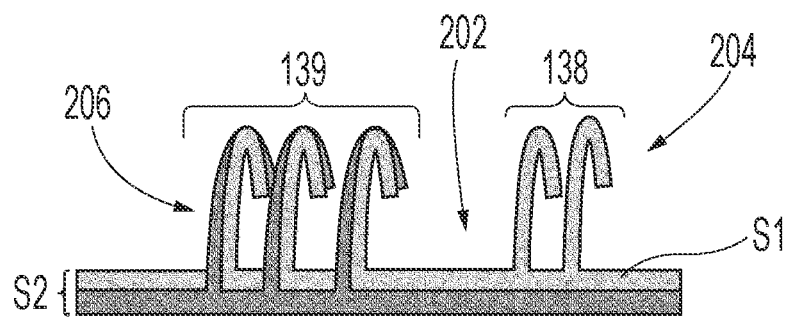
Figure 5F:
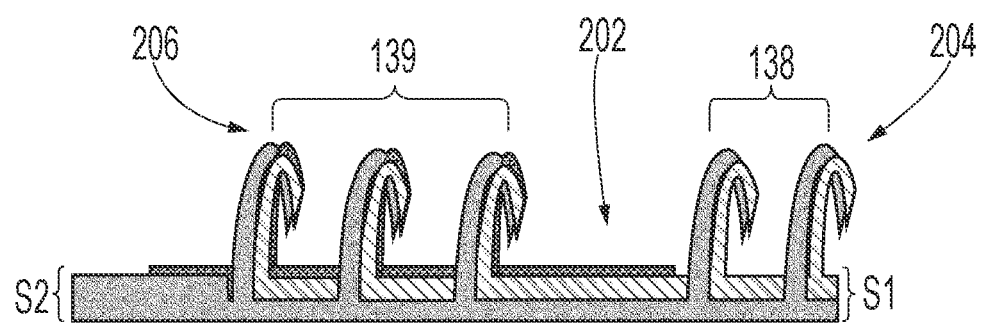
Figure 5G:
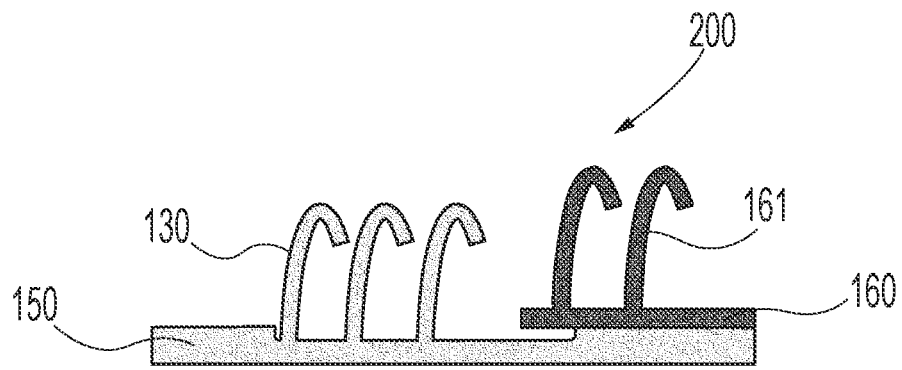

In some embodiments, the fastening component may comprise both integral fastening elements 130 and non-integral fastening elements 161 that are disposed on a discrete patch of material 160 joined to an article component as shown in FIG. 5G. The discrete patch of material may comprise a nonwoven, an extensible material such as a film, or combinations thereof.

Figure 5H:
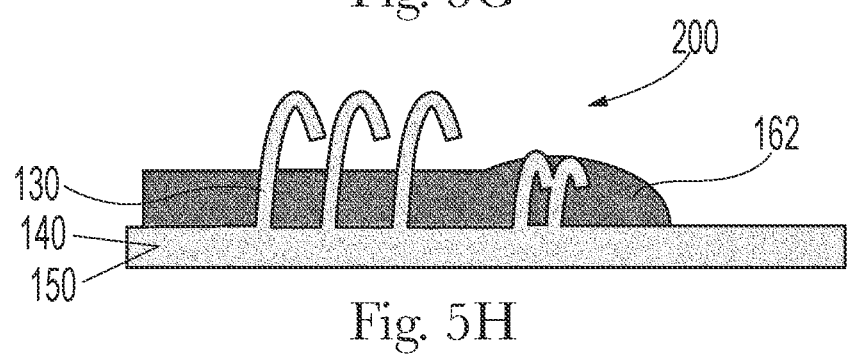
Figure 5I:
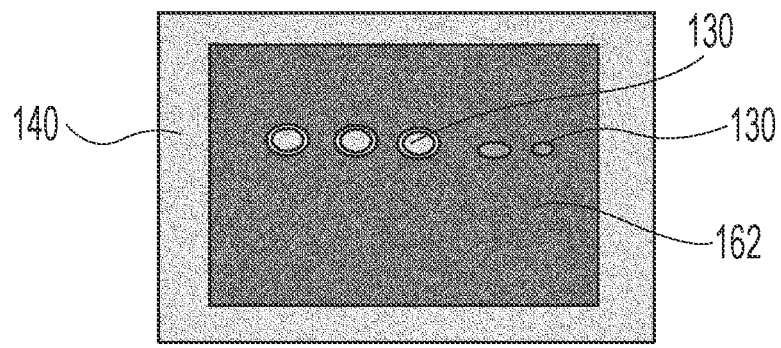
FIG. 5I is a schematic plan view of an exemplary hook configuration.
Figure 5J:
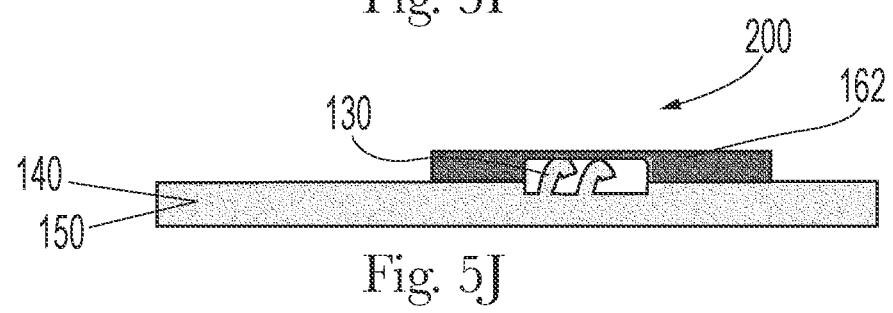
FIG. 5J is a schematic side elevation view of an exemplary hook configuration.

Turning to FIG. 5H, the overlapping region 200 may comprise one or more material layers from which integral fastening elements 130 are formed and one or more secondary layers 162 that do not form a portion of the integral fastening elements. For instance, integral fastening elements may be formed from a first material layer 140. In some embodiments, a secondary layer may subsequently be added to the region 200. The secondary layer may comprise a film, nonwoven, polyolefin, adhesive, hotmelt composition (e.g., hotmelt adhesive, metallocene-catalyzed polymers (e.g., LICOCENE® from Clariant)), ink, dye, tactile modifier, lotion and combinations thereof. The secondary layer may be added to the substrate while in a molten, or otherwise flowable, state. The secondary layer 162 may be in facing relationship with at least a portion of the integral fastening elements. Additionally, or alternatively, a portion of the secondary layer may surround the base of one or more fastening elements as shown in FIGS. 5H and 5I. At least a portion of the integral fastening elements may extend between the first material layer and the secondary layer as depicted in FIG. 5J. At least a portion of the integral fastening elements may extend through the thickness of the secondary layer(s), and/or at least a portion of the fastening elements may extend above or through the secondary layer as shown in FIG. 5H. It is also contemplated that one or more fastening elements 114 may be formed from the secondary layer 162, and the overlapping region may comprise discrete fastening elements interspersed with integral fastening elements 130.

It is also contemplated that mechanical bonds, compressed areas, and/or embossed areas may be present in the overlapping region.

Returning to FIGS. 5A-5B, the overlapping region 200 may comprise an opacity that is lower than an adjacent area 202 of the article component. In some nonlimiting examples, the opacity of the adjacent region is about 25% greater, or about 30% greater or about 50% greater, or from about 25% to about 100% greater than the opacity of the overlapping region as determined by the Opacity Test Method. In non-limiting examples, a first plurality of fastening elements 138 may be disposed in a first overlapping section 204 and a second plurality of fastening elements 139 may be disposed in a second overlapping section 206 as illustrated in FIGS. 5E and 5F. The first overlapping section may comprise a first opacity and the second overlapping section 206 may comprise a second opacity, which may differ from the first opacity. The first and second opacity values may differ by about 25%, or about 30% or about 50%, or from about 25% to about 100% as determined by the Opacity Test Method.

Additionally, or alternatively, the opacity of the adjacent area 202 may be about 25% greater, or about 30% greater or about 50% greater, or from about 25% to about 100% greater than the first and/or second opacity as determined by the Opacity Test Method.

Figure 6A:
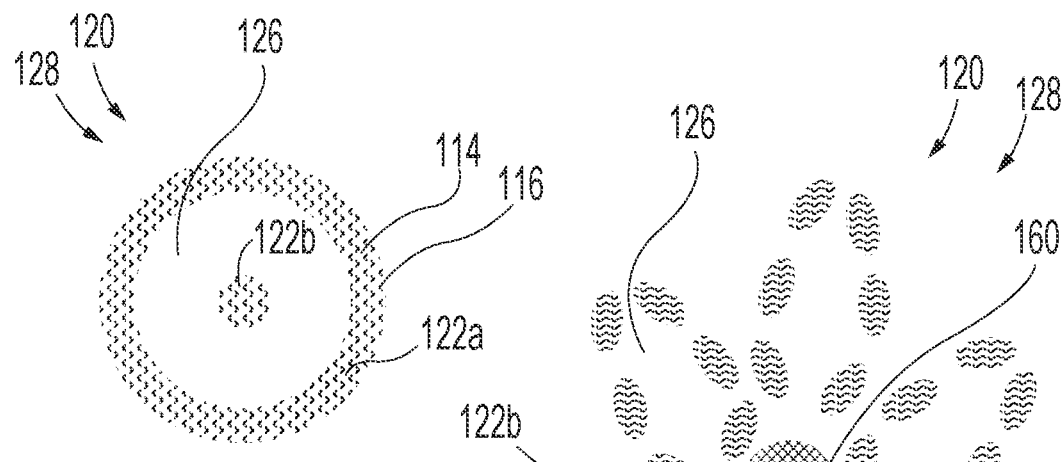
FIGS. 6A-6C are schematic depictions of various examples of macro patterns of fastening elements.
Figure 6B:
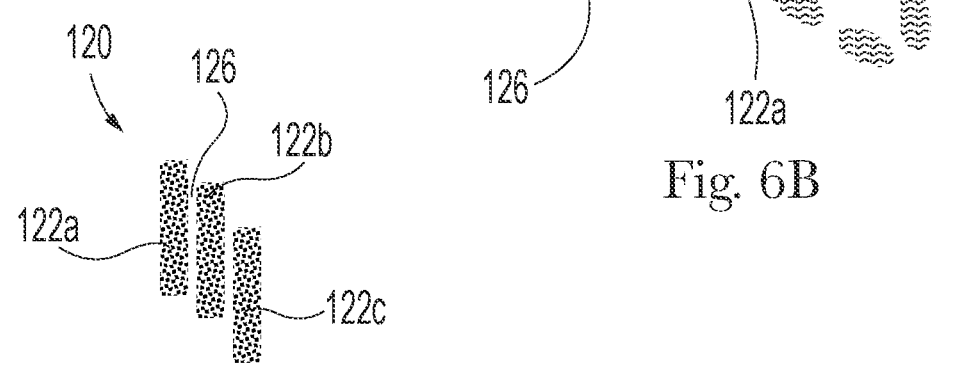
Figure 6C:
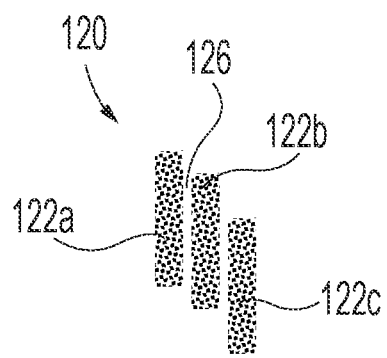

Using the molding process described above, the practical constraints and/or costs presented by supply and application of a continuous strip of pre-manufactured hooks material are eliminated, and the areas of fastening elements may be provided on the nonwoven material in any desired configuration, such as the configurations reflected in FIGS. 6A-6C. It can be appreciated that areas of fastening elements may be configured in any desired size, shape, pattern, directionality of hooks, number of hooks, or orientation. An orientation of an area of hooks is the angle of a line passing through the maximum dimension of the area with respect to the longitudinal axis of the article, as is discussed in more detail below.

By way of nonlimiting examples, areas of fastening elements may be disposed in lines, rectangular shapes and/or shapes formed from curvilinear sections. Areas of fastening elements may be configured as discrete, discontinuous shapes entirely surrounded by areas not occupied by fastening elements, as may be seen in FIGS. 6B-6C (sometimes known as "islands-in-the-sea" configurations). Continuous areas of fastening elements may be configured to entirely surround discrete, discontinuous shapes of areas not occupied by fastening elements, as may be seen in FIG. 6A.

Further to the above, integral fastening elements may be formed with varying directionality to provide different benefits in different sections of the component. For instance, hooks which are asymmetric about their vertical centerline (e.g., the inverted J-shape shown in FIGS. 5A-5G or similar hook configuration) may be formed so that the open portion is pointed in the direction of expected engagement. In further nonlimiting examples, hooks in a front waist region 14 may be imparted with directionality approaching or along the lateral direction and extending toward the longitudinal axis of the diaper. Such directionality provides mechanical structure extending in a direction opposite the ordinary direction of shear forces (directed away from the longitudinal axis in the front region) that would be exerted on the hooks in that region while the hooks are engaged during wear, providing for added fastening strength and/or more secure attachment, as compared with non-directional hooks of similar size, material utilization (shape volume) and numerical density. Hooks in the rear waist region may be imparted with directionality toward the longitudinal axis of the diaper (when the fastening member is in the open position). Such directionality would oppose the ordinary direction of shear forces that would be exerted on the hooks in the front waist region when the hooks are engaged (i.e., fastened) during wear, providing for added fastening strength and/or more secure attachment, as compared with non-directional hooks of similar size, material utilization (shape volume) and numerical density. It is also contemplated that fastening elements in one array may differ in direction from those of another array.

Figure 7A:
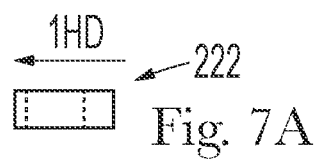
FIGS. 7A-7C, 8A-8C, and 9A-9C depict front, side and top views of examples of profiles of hooks protruding from a substrate.
Figure 7B:
Figure 7C:
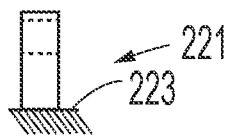
Figure 8A:
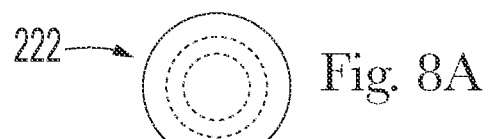
Figures 8B, 8C:
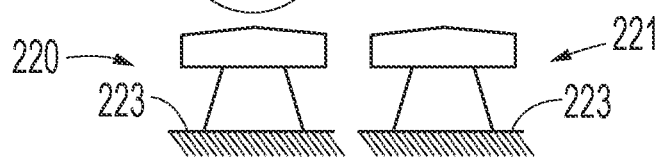
Figure 9A:
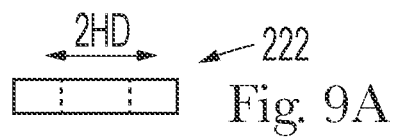
Figure 9B:
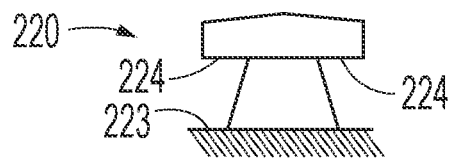
Figure 9C:
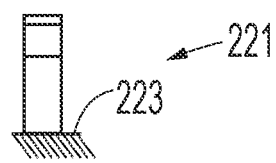

Exemplary hook shapes are shown in FIGS. 7A-9C. Each of FIGS. 7A-9C depicts a front view 220, side view 221 and top view 222 of one of three non-limiting examples of hook shapes, protruding or emerging from a substrate 223. (Substrate 223 may comprise the material layer(s) as described above, from which the hooks are integrally formed.) The hook shape example reflected in FIGS. 7A-7C is substantially unidirectional in that it hooks over predominately in one direction 1HD. However, as described above, the direction hooks in one array may be different from the direction in another array or another area of the article. Referring to FIGS. 8A-8C, this type of hook shape (sometimes described as a "mushroom" shape) lacks directionality because it is substantially symmetrical about all planes along its vertical (z-direction) axis and/or has substantially similar front and side view profiles. Other types of hook shapes may be formed to have directionality such that they lack such symmetry and/or similarity of front and side views. The hook shape reflected in FIGS. 9A-9C (sometimes described as an "arrowhead" shape) is substantially bi-directional in that it has two opposing arms 224 that hook over in two opposite directions 2HD.

The flexibility in the above-mentioned process permits more precise placement of fastening elements to effectuate certain properties (e.g., greater bond strength) in certain areas. Returning to FIGS. 4 and 6A-6C, in certain embodiments, the fastening elements may be disposed in a macro pattern 120 having a plurality of arrays 122, including a first array 122a and a second array 122b of fastening elements. The macro pattern may optionally include additional arrays, such as a third array 122c. An array of fastening elements is a plurality of fastening elements wherein each element is no more than about 2 mm, or from about 0.1 mm to about 2 mm, or from about 0.5 mm to about 1.5 mm from at least one of the other elements in the plurality, reciting for each range every 0.1 mm increment therein. A macro pattern comprises at least two arrays of fastening elements, wherein each array is spaced from at least one other array by 2 mm or more, or about 2.25 mm or more, or about 35 mm or less, or about 30 mm or less, or about 25 mm or less, or about 15 mm or less, from about 2.25 mm to about 35 mm, or from about 3 mm to about 30 mm, or from about 2.5 mm to about 25 mm, or from about 3 mm to about 20 mm, or from about 4 mm to about 15 mm, reciting for each range every 1 mm increment therein. A void area 126 (i.e., areas free of fastening elements) separates arrays. Arrays of fastening elements, or a macro pattern, may form a line, a curve, a geometric shape, a non-geometric shape, design element 128 and/or may form a closed shape surrounding a region free of fastening elements 126. Spacing and shape of individual arrays within a macro pattern may be the same or different in different portions of the macro pattern.

Arrays may differ from one another in any of the following characteristics: peel strength, shapes of fastening elements, the number of fastening elements, types of fastening elements (e.g., hooks, tabs), directionality of fastening elements, orientation of array, average spacing of fastening elements, whether the elements are discrete or integral or some combination, fastening element constituent materials (i.e., the material(s) from which the elements are made such as nonwoven, films and combinations thereof), the number and/or types of layers from which integral fastening elements are formed, average size of the fastening elements, aggregate shape of the array, surface area, opacity, color and combinations thereof. A first array 122a may surround a second array 122b as indicated in FIG. 6A for example. The second array 122b may be disposed laterally inboard of the first array 122a, and/or longitudinally inboard of the first array or vice versa.

A macro pattern may comprise a maximum width, Wp. The maximum width, Wp, is the distance between the laterally furthest apart fastening elements as illustrated in FIG. 4. The maximum width of the macro pattern, Wp, may be at least about 10% of the width of the article component 150 along a line K extending through the longitudinal center of the macro pattern 120 and parallel to the lateral axis of the article. It may be desirable that the macro pattern is at least about 20%, or at least about 40%, or at least about 50%, or at least about 60%, or from about 10% to about 100%, or from about 25% to about 75%, or from about 30% to about 60% of the width of the article component 150 at line K.

The macro pattern may comprise at least about 20%, or at least about 40%, or at least about 50%, or at least about 60%, or at least about 75%, or about 100% of integrally formed fastening elements 130 based on the number of fastening elements. In nonlimiting examples, the macro pattern comprises both integrally formed fastening elements 130 and discrete, non-integral fastening elements 161. For instance, the first array may comprise integrally formed hooks 130, and the second array may comprise non-integral fastening elements 161 on a discrete patch 160 joined to the article component 150, as suggested by FIGS. 5G and 6B.

Figure 10:
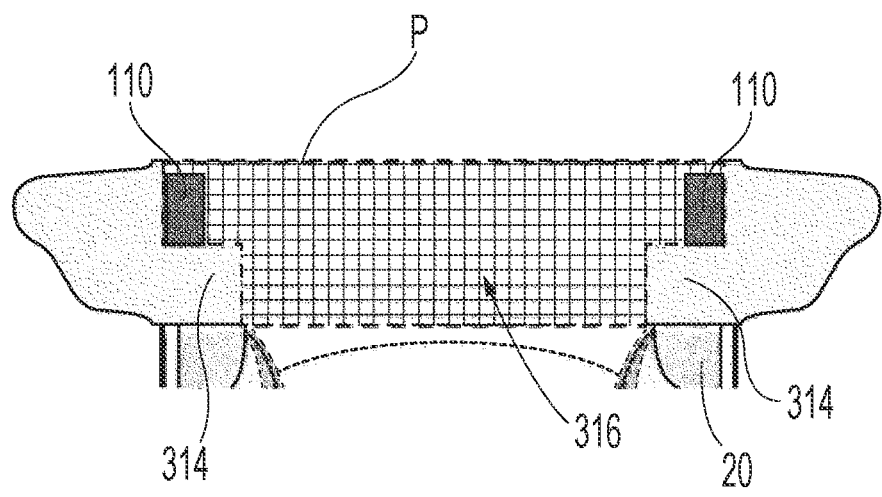
FIG. 10 is a schematic plan view of an exemplary composite with layers removed to illustrate an exemplary anchoring zone.

Turning to FIG. 10, the article may comprise an anchoring zone 316 wherein layers of the article are joined and one or more decoupled zones 314 said layers are unattached, attached in a weaker manner or attached in a more extensible manner (e.g., activated to be more extensible) than in the anchoring zone. A decoupled zone may be laterally and/or longitudinally inboard of a fastening component. The anchoring zone 316 is bounded by a perimeter P. Outside of said perimeter, layers may be unattached, attached in a weaker and/or more extensible manner than in the anchoring zone (e.g., activated to increase extensibility), thereby creating a decoupled zone 314. The perimeter may comprise substantially straight portions and/or curvilinear portions. In some nonlimiting examples, straight portions may be disposed at angle of 5-89° with respect to the lateral or longitudinal axis. The fastening component 110 may be at least partially disposed in the anchoring zone 316, thereby helping to ensure the fastening component is fixed in the desired position during application and wear. In nonlimiting examples, at least about 10%, or at least about 20%, or at least about 25%, or at least about 30%, or from about 10% to about 100%, or from about 25% to about 100% of the area of the fastener is located within the anchoring zone, reciting for each range every 5% increment therein. If the fastening component fully overlies a decoupled zone, said fastening component may be more prone to movement, allowing for an edge and/or the surface of the component to contact the skin. By reducing the overlap between the fastening component and the decoupled zone, flexibility may be achieved without increasing the likelihood of skin irritation.

Without being bound by theory, it is believed that the decoupled zone may move independently of surrounding materials or with greater flexibility than surrounding materials, reducing the effects of the tension that arises from exudate loading. During use, a tension line forms in the article between the load, located between the wearer's thighs in the crotch region, and a fastener (particularly a front fastening component), located proximate to the wearer's hip. In typical attachment configurations, material outboard of the tension line collapses, folds or otherwise deforms as the article narrows to fit the wearer's body. When continuously attached, substantially all material surrounding the fastening component folds or collapses, such that it is relocated to behind the fastening component which may result in the fastening component being placed in contact with the wearer's skin. It is believed that the decoupled zone lessens the effects of the tension line by permitting the composite or certain composite layers to operate independently in the zone. The anchoring zone 316 continues to provide the necessary bonding between the composite layers while the decoupled zone permits layers to operate more independently of the tension. While the chassis may deform about the body, the decoupling prevents materials surrounding the fastening component from being forced to move with the chassis, thereby reducing the tendency to collapse, fold or otherwise deform.

Where multiple fastening systems are provided on the article, they may differ in peel strength, macro patterns (including the presence or absence of a macro pattern), types of hook shapes (if applicable), directionality of fastening elements, size of fastening and/or receiving components, types of fastening elements (e.g., hooks, adhesive), types of receiving components, fastening component type (i.e., integral or discrete or combination), receiving component type (i.e., integral or discrete or combination), location of fastening and/or receiving components and combinations thereof. Where multiple fastening components each comprise macro patterns, the macro patterns may differ by peel strength, design element, surface area, opacity, color, array characteristics noted above, combination of arrays, spacing of arrays from one another, relative positioning of arrays, the number of arrays and combinations thereof. In nonlimiting examples, a primary fastening system and second fastening system may comprise the same type of fastening mechanism (e.g., hook-and-loop) with different material combinations, such that the primary and secondary fastening systems differ in peel strength, integrity after release (i.e., less disruption to the fastening elements and/or receiving components after disengagement), or combinations thereof.

Waist Features

Returning to FIG. 1, the absorbent article 10 may comprise at least one waist feature 40 that helps to provide improved fit and containment, as shown in FIG. 1. In some nonlimiting examples, one or both of the article's waist edges 13, 19 may be at least partially defined by a waist feature. In further nonlimiting examples, a waist feature may be disposed inboard of the closest waist edge. A waist feature may be integral with one or more layers of the chassis, cuffs and/or other elements in the waist region, or may be discrete and joined to one or more layers of the chassis, leg cuff structures and/or other elements disposed in the waist region. The waist feature may be joined between layers, on the outward-facing surface 11 of the article, or on the wearer-facing surface 9 of the article. The waist feature may be extensible or elastic. An elasticized waist feature 42 is generally intended to expand and contract to dynamically fit the wearer's waist. Elasticized waist features include waistbands, waist cuffs having pockets formed from a portion of the waist feature 40 that is unattached from the chassis 20, belts 44 extending through the waist region and beyond longitudinal edges of the chassis, and waist panels designed to fit securely about the abdomen of the wearer. Nonlimiting examples of elasticized waist features are disclosed in U.S. patent application Ser. Nos. 13/490,543; 14/533,472; and 62/134,622. Elasticized waist features may comprise one or more nonwoven layers and one or more elastic elements 45. In nonlimiting examples, the elasticized waist feature comprises elastic strands joined to the nonwoven layer(s). In further nonlimiting examples, the elasticized waist feature comprises a laminate of one or more nonwoven layers and one or more films.

In alternative embodiments, the waist feature may be inelastic. In such configurations, the waist feature may provide additional anchoring about the waist of the wearer.

Waist features 40 may be joined to the chassis 20 in the first waist region 14 and/or in the second waist region 18. The waist feature can be used in conjunction with the ear 30 to provide desirable stretch and flexibility for proper fit of the article on the wearer.

Leg Gasketing Systems

Still referring to FIG. 1, the absorbent article 10 may comprise a leg gasketing system 70 attached to the chassis 20, which may comprise one or more cuffs. The leg gasketing system may comprise a pair of barrier leg cuffs 72. Each barrier leg cuff may be formed by a piece of material which is bonded to the absorbent article so it may extend upwards from a wearer-facing surface of the absorbent article and provide improved containment of fluids and other body exudates approximately at the junction of the torso and legs of the wearer. The barrier leg cuffs are delimited by a proximal edge joined directly or indirectly to the topsheet 24 and/or the backsheet 26 and a free terminal edge 75, which is intended to contact and form a seal with the wearer's skin. In some embodiments, the free terminal edge 75 comprises a folded edge. The barrier leg cuffs 72 extend at least partially between the front waist edge 13 and the rear waist edge 19 of the absorbent article on opposite sides of the longitudinal centerline 90 and are at least present in the crotch region. The barrier leg cuffs may be joined at the proximal edge with the chassis of the article by a bond which may be made by gluing, fusion bonding, or a combination of other suitable bonding processes.

The barrier leg cuffs may be integral with the topsheet 24 or the backsheet 26 or may be a separate material joined to the article's chassis. Each barrier leg cuff 72 may comprise one, two or more elastic elements 55 close to the free terminal edge 75 to provide a better seal.

In addition to the barrier leg cuffs 72, the article may comprise gasketing cuffs 76, which are joined to the chassis of the absorbent article, in particular to the topsheet 24 and/or the backsheet 26 and are placed externally relative to the barrier leg cuffs 72. The gasketing cuffs 76 may provide a better seal around the thighs of the wearer. A gasketing cuff may comprise a proximal edge and a free terminal edge 77. The free terminal edge 77 may comprise a folded edge. Each gasketing cuff may comprise one or more elastic elements 55 in the chassis of the absorbent article between the topsheet 24 and backsheet 26 in the area of the leg openings. All, or a portion of, the barrier leg cuffs and/or gasketing cuffs may be treated with a lotion or another skin care composition.

In further embodiments, the leg gasketing system comprises barrier leg cuffs that are integral with gasketing cuffs. Suitable leg gasketing systems which may be part of the absorbent article are disclosed in U.S. Pat. App. No. 62/134, 622, 14/077,708; U.S. Pat. Nos. 8,939,957; 3,860,003; 7,435,243; 8,062,279.

Combinations

A. An absorbent article comprising:
      a topsheet, a backsheet, and an absorbent core disposed between the topsheet and backsheet;
      a first waist region, a second waist region and a crotch region disposed between the first and second waist region; and
      a fastening system comprising a fastening component disposed on an article component, wherein at least two layers overlap at least a portion of the fastening component and wherein the fastening component comprises a first plurality of fastening elements integrally formed from a first set of layers and a second plurality of fastening elements integrally formed from a second set of layers.

B. The absorbent article of paragraph A, wherein the article component is selected from the backsheet, an ear, a landing zone, a fastener attachment arm, a belt or combinations thereof.
C. The absorbent article of paragraphs A or B, wherein the at least two layers comprise a polyolefin, adhesive, ink, tactile modifier, dye or combinations thereof.
D. The absorbent article of any of the preceding paragraphs, wherein the first plurality of fastening elements comprise hooks.
E. The absorbent article of any of the preceding paragraphs, wherein the first plurality of fastening elements comprise a difference in opacity from the article component as compared to an area immediately adjacent to the first plurality of fastening elements.
F. The absorbent article of any of the preceding paragraphs, wherein the first set of layers comprises a nonwoven and a film.
G. The absorbent article of any of the preceding paragraphs, wherein the first and second set of layers have at least one layer in common and at least one layer that is different.
H. The absorbent article of any of the preceding paragraphs, wherein the first plurality of elements comprises a first directionality and the second plurality comprises a second directionality, wherein the first and second directionalities are different.
I. The absorbent article of any of the preceding paragraphs, further comprise one or more fastening elements disposed on a discrete patch joined to the article component.
J. The absorbent article of paragraph I, wherein the discrete patch comprises a nonwoven, film or combinations thereof.
K. The absorbent article of any of the preceding paragraphs, wherein the at least two layers comprise a first material layer and a secondary layer, and the first plurality of fastening elements is integrally formed from the first material layer but not from the secondary layer.
L. The absorbent article of paragraph K, wherein none of the fastening elements in the first and second pluralities are integrally formed from the secondary layer.
M. The absorbent article of paragraphs K or L, wherein the secondary layer comprises a polyolefin, adhesive, hotmelt composition, film, ink, tactile modifier, dye or combinations thereof.
N. The absorbent article of any of paragraphs K-M, wherein at least some of the fastening elements of the first plurality and/or fastening elements of the second plurality extend between the first material layer and the secondary layer.
O. The absorbent article of any of paragraphs K-N, wherein the secondary layer is surrounds one or more of the integrally formed fastening elements.
P. The absorbent article of any of paragraphs K-O, wherein the secondary layer comprises one or more fastening elements that are discrete from the first material layer.
Q. The absorbent article according to any of paragraphs K-P where the one or more fastening elements of the secondary layer are interspersed with the integral fastening elements.
R. An absorbent article comprising:
a topsheet, a backsheet, and an absorbent core disposed between the topsheet and backsheet; a first waist region, a second waist region and a crotch region disposed between the first and second waist region; and
a fastening system comprising a fastening component disposed on an article component, wherein at least two layers overlap at least a portion of the fastening component and wherein the fastening component comprises a first plurality of elements integrally formed from a first set of layers and a second plurality of elements disposed on a discrete patch.
S. The absorbent article of paragraph R, wherein the discrete patch comprises a nonwoven.
T. The absorbent article of paragraphs R or S, wherein the discrete patch comprises a film.
U. The absorbent article of any of paragraphs R-T, wherein a micropattern comprises the first and second pluralities of elements.
V. The absorbent article of any of paragraphs R-U, wherein the at least two layers comprise a polyolefin, film, adhesive, ink, tactile modifier, dye or combinations thereof.

Test Methods
Hysteresis Test

The following test methods utilize a commercial tensile tester (e.g., from Instron Engineering Corp. (Canton, Mass.), SINTECH-MTS Systems Corporation (Eden Prairie, Minn.) or equivalent) interfaced with a computer. The computer is used to control the test speed and other test parameters and for collecting, calculating, and reporting the data. The tests are performed under laboratory conditions of 23 deg. C.+−2 deg. C. and relative humidity of 50%+−2%. The samples are conditioned for 24 hours prior to testing.

1. Select a 2.54 cm (width), 7.62 cm (length) sample of the material for testing. In some cases, if it is not be possible to get a 2.54 cm×7.62 cm sample, a smaller sample may be used, but a gage length of 25 mm must still be used. If the sample is activated or includes an activation portion, the length of the sample is taken in the direction of activation.

2. Select the appropriate jaws and load cell. The jaws must have flat surfaces and must be wide enough to fit the sample (e.g., at least 2.54 cm wide). Also, the jaws should provide adequate force to ensure that the sample does not slip during testing. The load cell is selected so that the tensile response from the sample tested is between 25% and 75% of the capacity of the load cell used.

3. Calibrate the tester according to the manufacturer's instructions.

4. Set the distance between the grips at 25 mm.

5. Place the sample in the flat surface of the jaws such that the longitudinal axis of the sample is substantially parallel to the gauge length direction. Mount the sample with minimal slack. Set the slack preload at 0.02 N/cm. This means that the data collection starts when the slack is removed with a force of 0.02 N/cm. Strain is calculated based on the adjusted gauge length (lini), which is the length of the sample in between the grips of the tensile tester at a force of 0.02 N/cm. This adjusted gauge length is taken as the initial sample length, and it corresponds to a strain of 0%. Percent strain at any point in the test is defined as the change in length divided by the adjusted gauge length times 100%.

6(a) First cycle loading: Pull the sample to a strain of 50% at a constant cross head speed of 254 mm/min.

6(b) First cycle unloading: Hold the sample at 50% strain for 30 seconds and then return the crosshead to its starting position (0% strain) at a constant cross head speed of 254 mm/min. Hold the sample in the unstrained state for 1 minute.

6(c) Set from second cycle loading: Pull the sample at a constant cross head speed of 254 mm/min, till it reaches a load of 0.05 N/25.4 mm (0.020 N/cm). Record the extended gauge length (lext). Next, return the crosshead to its starting position (zero strain) at a constant cross head speed of 254 mm/min. Set is defined as the strain at a second cycle load of 0.05 N/25.4 mm (0.020 N/cm). Calculate % set as indicated below.

6(d) Second cycle unload: Next, return the crosshead to its starting position (zero strain) at a constant cross head speed of 254 mm/min.

Percent Set is defined as the percent strain at a second cycle load of 0.05 N/25.4 mm (0.020 N/cm). Calculate % set as indicated below.

A computer data system records the force exerted on the sample during the test as a function of applied strain. From the resulting data generated, the following quantities are reported (note that loads are reported as force divided by the width of the sample and do not take into account the thickness of the sample):
1. Loads at 25% strain and 50% strain (N/cm)
2. % set (Percent Strain measured at a second cycle load of 0.02N/cm);
3. % set=(lext-lini)/lini*100%.

Five repetitions are done on each sample and the average and standard deviation reported.

The Hysteresis Test can be suitably modified depending on the expected attributes and/or properties of the particular material sample to be measured. For example, the Test can be suitably modified where a sample of the length and width specified above are not available from the subject article.

Opacity Test Method

Opacity by contrast ratio measurements are made using a 0°/45° spectrophotometer suitable for making standard CIE L*a*b* color measurements (e.g. Hunterlab Labscan XE spectrophotometer, Hunter Associates Laboratory Inc., Reston VA or equivalent). The diameter of the instrument's measurement port should be chosen such that only the region of interest is included within the measurement port. Analyses are performed in a room controlled at about 23° C.±2° C.° and 50%±2% relative humidity. Samples are conditioned at the same condition for 2 hours before testing.

Calibrate the instrument per the vendor instructions using the standard black and white tiles provided by the vendor. Set the spectrophotometer to use the CIE XYZ color space, with a D65 standard illumination and 10° observer. Using cryogenic spray and scissors carefully excise the specimen from the article for testing. Where the area of interest is an overlapping region 200, the specimen is to include the fastening hooks and the layers from which they are formed (if applicable) and the layer to which they are attached. The adjacent area should include the same layers. Place the specimen flat against the instrument with the outward facing surface toward the spectrophotometer's measurement port and the region of interest within the port. Ensure that no tears, holes or apertures are within the measurement port. Place the white standard tile onto the opposing surface of the specimen such that it completely covers the measurement port. Take a reading for XYZ and record to 0.01 units. Without moving the specimen, remove the white plate and replace it with the black standard plate. Take a second reading for XYZ and record to 0.01 units. Repeat this procedure at a corresponding site for a total of ten (10) replicate specimens.

Opacity is calculated by dividing the Y value measured using the black tile as backing, divided by the Y value measured using the white tile as backing. Record the opacity value to the nearest 0.001. Calculate opacity for the 10 replicates for the sample and report the average opacity to the nearest 0.001.

The difference between an opacity of a first sample and a second sample is calculated using the following equation:

$$\% \text{ Difference} = \text{average opacity for sample 1} - \text{average opacity of sample 2}/\text{average opacity of sample 2} * 100\%$$

wherein sample 2 is the sample having the lower of the two average opacities.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   a topsheet, a backsheet, and an absorbent core disposed between the topsheet and backsheet:
   a first waist region, a second waist region and a crotch region disposed between the first and second waist region; and
   a fastening system comprising a fastening component disposed on an article component, wherein at least two layers overlap at least a portion of the fastening component, wherein the at least two layers forming a first set of layers and a second set of layers, and wherein the fastening component comprises a first plurality of fastening elements integrally formed from each layer of the first set of layers and a second plurality of fastening elements integrally formed from the second set of layers.

2. The absorbent article of claim 1 wherein the article component is selected from the backsheet, an ear, a landing zone, a fastener attachment arm, a belt or combinations thereof.

3. The absorbent article of claim 1 wherein the at least two layers comprise a polyolefin, adhesive, ink, tactile modifier, dye or combinations thereof.

4. The absorbent article of claim 1 wherein the first plurality of fastening elements comprise hooks.

5. The absorbent article of claim 1 wherein the first plurality of fastening elements has a first opacity, wherein an area immediately adjacent to the first plurality of fastening elements has a second opacity, and wherein the first opacity is different than the second opacity.

6. The absorbent article of claim 1 wherein the first set of layers comprises a nonwoven and a film.

7. The absorbent article of claim 1 wherein the first and second set of layers have at least one layer in common and at least one layer that is different.

8. The absorbent article of claim 1 wherein the first plurality of fastening elements comprises a first directionality and the second plurality of fastening elements comprises a second directionality, wherein the first and second directionalities are different.

9. The absorbent article of claim 1, wherein the fastening system further comprises a receiving component, wherein the fastening component and the receiving component are disposed in the first waist region or the second waist region.

10. The absorbent article of claim 9, wherein the fastening component is configured to engage with the receiving component.

11. The absorbent article of claim 1, wherein the first plurality of fastening elements and the second plurality of fastening elements differ from one another in at least one of: peel strength, shape of fastening elements, orientation of fastening elements, average spacing of fastening elements, average size of fastening elements, opacity, color, and combinations thereof.

12. An absorbent article comprising:
 a topsheet, a backsheet, and an absorbent core disposed between the topsheet and backsheet;
 a first waist region, a second waist region and a crotch region disposed between the first and second waist region;
 a first fastening system comprising a first fastening component disposed on an article component, wherein at least two layers overlap at least a portion of the first fastening component, wherein the at least two layers forming a first set of layers and a second set of layers, and wherein the first fastening component comprises a first plurality of fastening elements integrally formed from each layer of the first set of layers and a second plurality of fastening elements integrally formed from each layer of the second set of layers; and
 a second fastening system comprising a second fastening component.

13. The absorbent article of claim 12, wherein the first fastening system is disposed in the first waist region, and the second fastening system is disposed in the second waist region.

14. The absorbent article of claim 12, wherein the first fastening system is disposed on a garment-facing surface of the absorbent article.

15. The absorbent article of claim 14, wherein the second fastening system is disposed on a wearer-facing surface of the absorbent article.

16. The absorbent article of claim 12, wherein the second fastening system comprises a third plurality of fastening elements, wherein the third plurality of fastening elements are integrally formed from the article component.

* * * * *